US009500583B2

(12) United States Patent
Jiang et al.

(10) Patent No.: US 9,500,583 B2
(45) Date of Patent: Nov. 22, 2016

(54) METHOD AND APPARATUS FOR MEASURING CARBON DIOXIDE DISSOLVED IN SOLUTION AND WELLBORE MONITORING SYSTEMS BASED THEREON

(76) Inventors: Li Jiang, Katy, TX (US); Terizhandur S. Ramakrishnan, Boxborough, MA (US); Timothy G. J. Jones, Cambridgeshire (GB); Roy Koveleski, Danbury, CT (US); Albert Perez, Jr., Brookfield, CT (US); Robert Kevin O'Leary, Newton, MA (US)

(*) Notice: Subject to any disclaimer, the term of this patent is extended or adjusted under 35 U.S.C. 154(b) by 388 days.

(21) Appl. No.: 13/104,388

(22) Filed: May 10, 2011

(65) Prior Publication Data

US 2012/0290208 A1    Nov. 15, 2012

(51) Int. Cl.
  *G01V 5/04* (2006.01)
  *G01N 21/552* (2014.01)
  *G01N 21/3504* (2014.01)

(52) U.S. Cl.
  CPC ........ *G01N 21/552* (2013.01); *G01N 21/3504* (2013.01); *G01N 2201/022* (2013.01); *G01N 2201/0218* (2013.01)

(58) Field of Classification Search
  CPC .................. G01J 5/02; G01N 21/00; G01N 21/552; G01N 21/3504; G01N 21/35
  USPC ..................................................... 250/341.8
  See application file for complete search history.

(56) References Cited

U.S. PATENT DOCUMENTS

| 5,473,161 | A  | * | 12/1995 | Nix et al. ....................... 250/343 |
| 6,218,662 | B1 |   | 4/2001  | Tchakarov et al. |
| 6,627,873 | B2 | * | 9/2003  | Tchakarov et al. ........... 250/256 |
| 6,662,116 | B2 |   | 12/2003 | Brown |
| 6,969,857 | B2 |   | 11/2005 | Owen |
| 6,995,360 | B2 |   | 2/2006  | Jones et al. |
| 7,812,312 | B2 | * | 10/2010 | Mantele et al. .............. 250/343 |
| 2007/0108378 | A1 | * | 5/2007 | Terabayashi et al. ........ 250/256 |
| 2007/0200065 | A1 | * | 8/2007 | Arno ............................. 250/343 |
| 2008/0078544 | A1 | * | 4/2008 | Christian et al. ............. 166/264 |
| 2008/0309922 | A1 |   | 12/2008 | Anders et al. |
| 2009/0302221 | A1 |   | 12/2009 | Tavernier et al. |
| 2011/0051125 | A1 |   | 3/2011  | Kim |
| 2012/0085144 | A1 | * | 4/2012  | Krolak et al. ................. 73/19.1 |
| 2013/0056626 | A1 |   | 3/2013  | Shen et al. |

FOREIGN PATENT DOCUMENTS

| EP | 1903329 A1 | 3/2008 |
| JP | 06341949   | 12/1994 |
| JP | 2000035399 | 2/2000 |
| WO | 0042416 A1 | 7/2000 |

(Continued)

OTHER PUBLICATIONS

Carroll, J. J., Slupsky, J. D., and Mather, A. E., "The Solubility of Carbon Dioxide in Water at Low Pressure," Journal of Physical and Chemical Reference Data, 1991, vol. 20(6): pp. 1201-1209.

(Continued)

*Primary Examiner* — Marcus Taningco
(74) *Attorney, Agent, or Firm* — Jakub Michna

(57) ABSTRACT

A sensing apparatus (and corresponding method) for monitoring carbon dioxide dissolved in a liquid solution employs a crystal surrounded in part by a sample chamber such that, in use, the liquid solution is in direct contact with the crystal.

50 Claims, 8 Drawing Sheets

(56) References Cited

FOREIGN PATENT DOCUMENTS

WO    0062028 A2    10/2000

OTHER PUBLICATIONS

Cotton, F. A., and Wilkinson, G., "Advanced Inorganic Chemistry, A Comprehensive Text," 4th Edition, John Wiley & Sons: New York, 1980: pp. 366-367.

Duan, Z., and Sun, R., "An Improved Model Calculating CO2 Solubility in Pure Water and Aqueous NaCl Solutions From 273 to 533 K and From 0 to 2000 Bar," Chemical Geology, 2003, vol. 193(3-4): pp. 257-271.

Halloway, S., Karimjee, A., Akai, M., Pipatti, R., and Rypdal, K., "Chapter 5: Carbon Dioxide Transport, Injection and Geological Storage," 2006 IPCC Guidelines for National Greenhouse Gas Inventories, Eds.: Eggleston et al., Intergovernmental Panel on Climate Change, 2006: pp. 5.1 to 5.32.

Hansen, J., Sato, M., Ruedy, R., Laois, A., and Oinas, V., "Global Warming in the Twenty-First Century: An Alternative Scenario," PNAS, Aug. 2000, vol. 97(18): pp. 9875-9880.

Extended Search Report of European Application No. 12167247.1 (60.1955EP) dated Nov. 23, 2012: pp. 1-7.

Cash et al. "Novel Online Sensor for Measuring Dissolved CO2 Using Attenuated Total Reflectance (ATR) Technology," 2007 ASBC Annual Meeting, Jun. 16-20, 2007, Fairmont Empress, Victoria, British Columbia, Canada, Thermal Fisher Scientific, 1 page.

O'Leary, et al. "Attenuated Total Reflection Spectroscopy method for measuring dissolved CO2 concentration in Beer," Published Aug. 2006, 9 pages.

"Spectral Calculator—Atmospheric Gas Spectra, Infrared Molecular Absorption Spectrum." SpectralCalc.com. GATS, Inc., May 28, 2010. Web. May 25, 2016, 1 page.

* cited by examiner

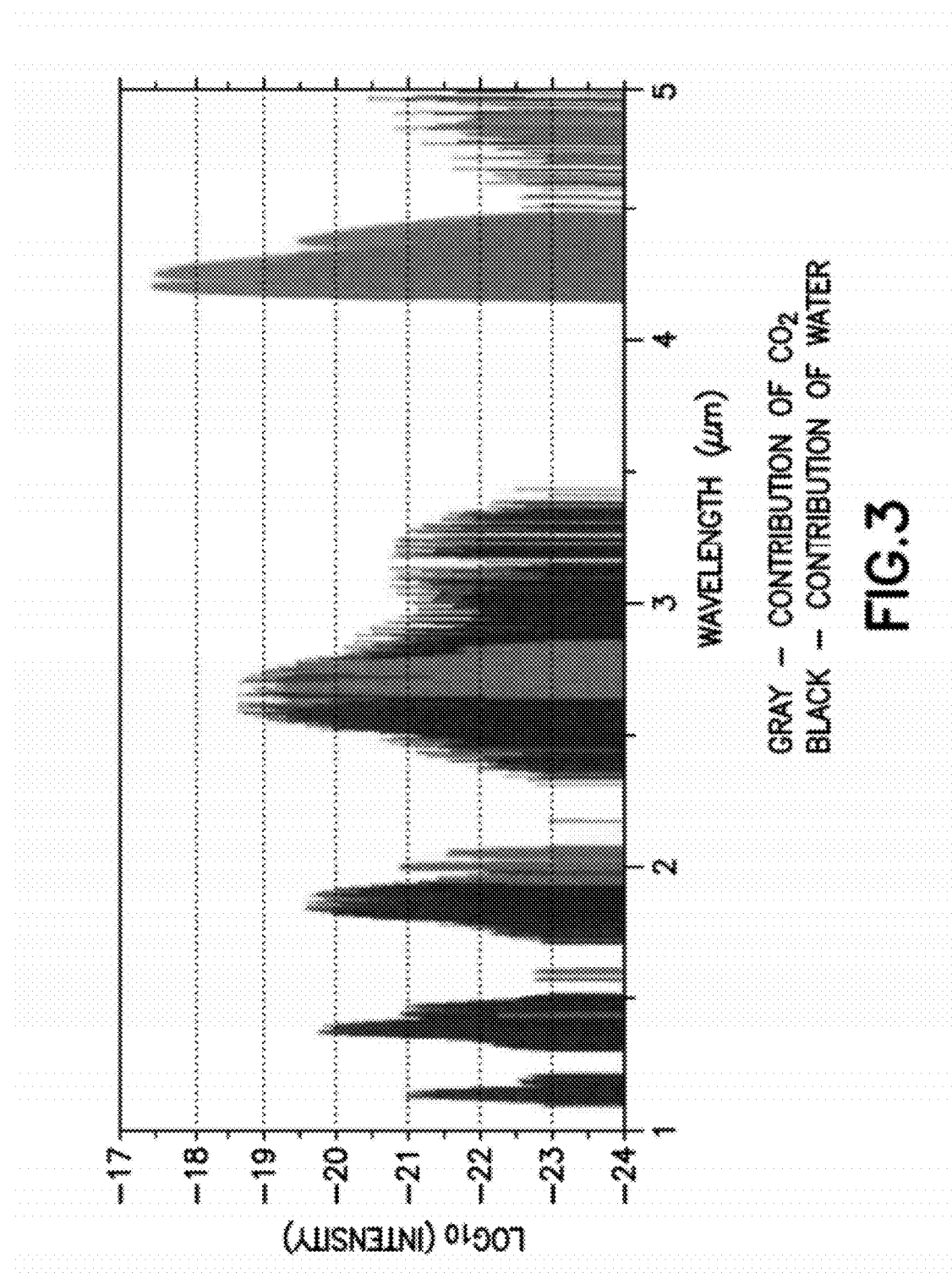

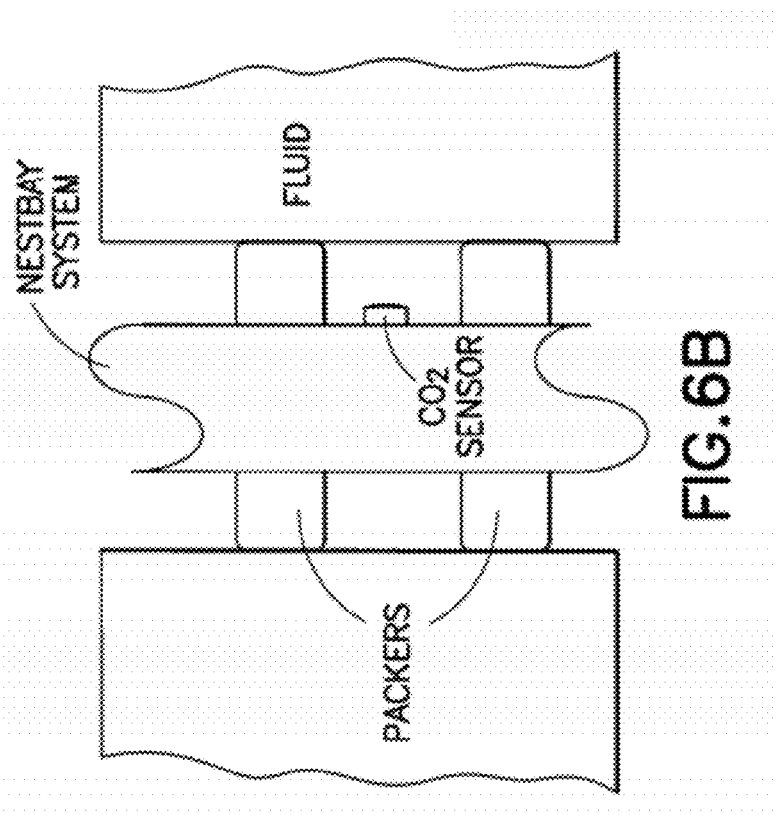
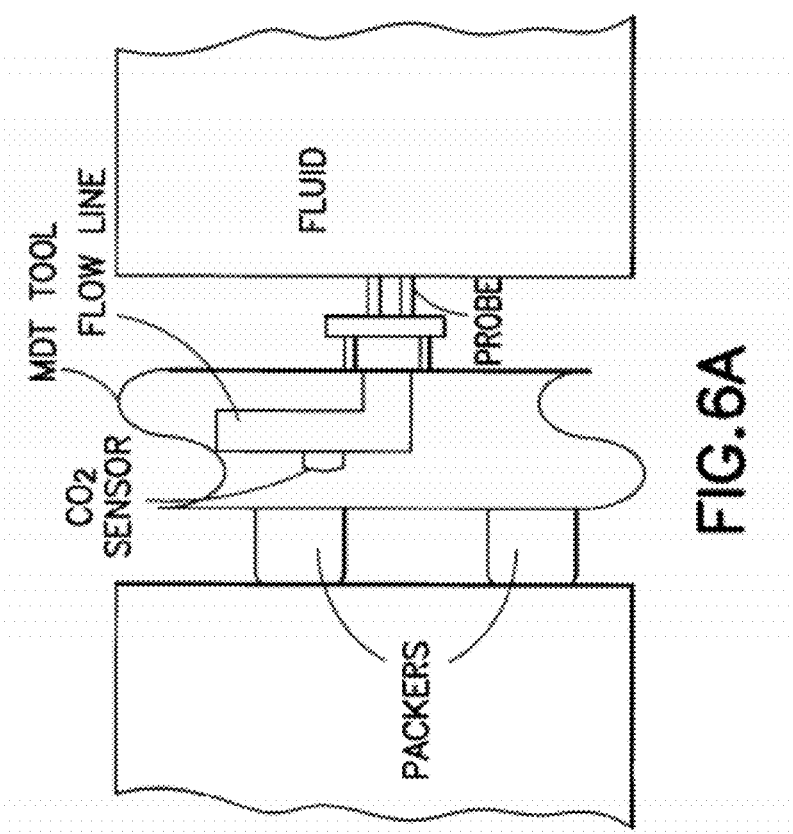

METHOD AND APPARATUS FOR MEASURING CARBON DIOXIDE DISSOLVED IN SOLUTION AND WELLBORE MONITORING SYSTEMS BASED THEREON

BACKGROUND OF THE INVENTION

Field of the Invention

This invention relates to measuring carbon dioxide ($CO_2$) dissolved in a solution. More particularly, this invention is related to the measuring of carbon dioxide dissolved in a solution after injection of carbon dioxide into a subterranean structure such as a saline aquifer.

State of the Art

At the current atmospheric concentrations, carbon dioxide is the largest contributor to radiative forcing in climate change. Atmospheric levels of carbon dioxide may be reduced through carbon dioxide capture, and injecting the captured carbon dioxide in geologically suitable sites. Among these sites, saline aquifers hold the highest promise for potential sequestration with a global storage capacity ranging from 1000 to 10,000 Gt (giga tonnes). In comparison, the annual anthropogenic emission of carbon dioxide is currently about 30 Gt (see IPCC report on underground geological storage).

Saline aquifers are subsurface geological formations consisting of water permeable rock that are saturated with brine. Super-critical carbon dioxide (i.e., carbon dioxide above critical pressure and temperature) can be injected into a saline aquifer via an injection well that extends into the saline aquifer. The injected carbon dioxide is retained in the saline aquifer via a combination of structural, residual, hysteretic, dissolution, and mineral storage mechanisms. For example, the injected carbon dioxide may either dissolve in the brine, react with the dissolved minerals or the surrounding rock, and/or become trapped in the pore space of the aquifer. Trapping occurs when carbon dioxide is surrounded by imbibing brine. Ideally, the saline aquifer has one or more layers of minimally porous and nearly impermeable rock (typically referred to as "cap-rock") that prevents water flow and the escape of the injected carbon dioxide. Typically, cement is used to plug the injection well after injection and monitoring phases are complete.

For verification, and any subsequent decision-making on possible mitigation operations, it is critical to be able to validate the integrity of the sequestration of the injected carbon dioxide within the saline aquifer, i.e., the injected fluid is within the zone of containment. Current technologies employ surface soil and air sampling in order to detect potential carbon dioxide leakage, whilst changes in the formation are monitored using seismic, electromagnetic, neutron, and fluid sampling based monitoring within the rock formations. Except for direct sampling based inferences, monitoring methods are affected by the presence of a carbon dioxide rich phase and are largely insensitive to carbon dioxide dissolved in a liquid phase. A carbon dioxide rich phase is typically not present over large parts of the saline aquifer at late times. Furthermore, the arrival of carbon dioxide in supercritical state is preceded by brine with dissolved carbon dioxide. It is therefore useful to have a method that allows one to directly quantify the amount of carbon dioxide within a liquid phase. Currently, a dissolved carbon dioxide sensor deployable at downhole conditions is unavailable.

SUMMARY OF THE INVENTION

In accord with the present invention, a sensing apparatus (and corresponding method) for monitoring of carbon dioxide dissolved in a liquid solution employs a crystal surrounded in part by a sample chamber such that, in use, the liquid solution is in direct contact with the crystal. An infrared light source directs at least one beam of infrared radiation into the crystal for at least one attenuated internal reflection at an interface between the crystal and the liquid solution. Infrared detection means detecting attenuated reflected infrared radiation produced by the crystal. Signal processing means measuring the intensity of the detected attenuated reflected infrared radiation. Data processing means determining the concentration of carbon dioxide dissolved in the liquid solution from the intensity of the detected attenuated reflected infrared radiation.

The apparatus and the method of using the apparatus are suitable for applications where the carbon dioxide is dissolved in a liquid solution (such as carbon sequestration in a subterranean brine aquifer).

The infrared source can be realized by a broadband infrared light source that generates a broadband infrared beam, and the infrared detection means can include a plurality of optical filters that provide bandpass optical filtering for predetermined infrared measurement bands. Preferably, the broadband infrared beam includes infrared radiation in a predetermined absorption band, infrared radiation in a predetermined reference band, and infrared radiation in an additional reference band, and the optical filters provide bandpass optical filtering in predetermined infrared measurement bands corresponding to the predetermined absorption band, the predetermined reference band, and the additional reference band (if necessary). The predetermined absorption band, which is most preferably centered around 4.27 μm, is selected such that carbon dioxide has a relatively high absorbance as compared to the absorbance of water for infrared radiation within the predetermined absorption band. The predetermined reference band, which is most preferably centered around 4.00 μm or 5.00 μm, is selected such that carbon dioxide and brine have minimal absorbance of infrared radiation within said predetermined reference band. The additional reference band is used to determine the presence of water in the fluid solution, and is preferably centered at or about 3.00 μm.

In the preferred embodiment, the data processing means employs a response model that relates intensities of the attenuated reflected infrared radiation in predetermined measurement bands to concentration of carbon dioxide dissolved in the liquid solution. For the case where carbon dioxide is dissolved in an aqueous solution (such as brine), the response model can be derived from a calibration process that measures a plurality of parameters and their temperature dependence. These include a parameter $k_1$, a parameter $k_2$, a parameter $k_4$ and a parameter $k_6$. The parameter $k_1$ is related to the absorbance of water in a predetermined reference band. The parameter $k_2$ is related to a reference intensity in the predetermined reference band and a reference intensity in a predetermined absorption band. The parameter $k_4$ is related to the absorbance of water in the predetermined reference band and in the predetermined absorption band. The parameter $k_6$ is related to the absorption coefficient of carbon dioxide dissolved in water. For the use of the sensor, it is convenient to express these parameters into two-temperature dependent coefficients $\alpha(T)$ and $\beta(T)$.

Additional objects and advantages of the invention will become apparent to those skilled in the art upon reference to the detailed description taken in conjunction with the provided figures.

BRIEF DESCRIPTION OF THE DRAWINGS

FIG. 3 is a graph of the absorption of carbon dioxide and water as a function of wavelength in the spectra range between 1 μm and 5 μm.

FIG. 6A is a schematic illustration of a first exemplary downhole logging tool that includes the sensor apparatus of the present invention.

FIG. 6B is a schematic illustration of a second exemplary downhole logging tool that includes the sensor apparatus of the present invention.

DETAILED DESCRIPTION OF THE PREFERRED EMBODIMENTS

Figure 1:
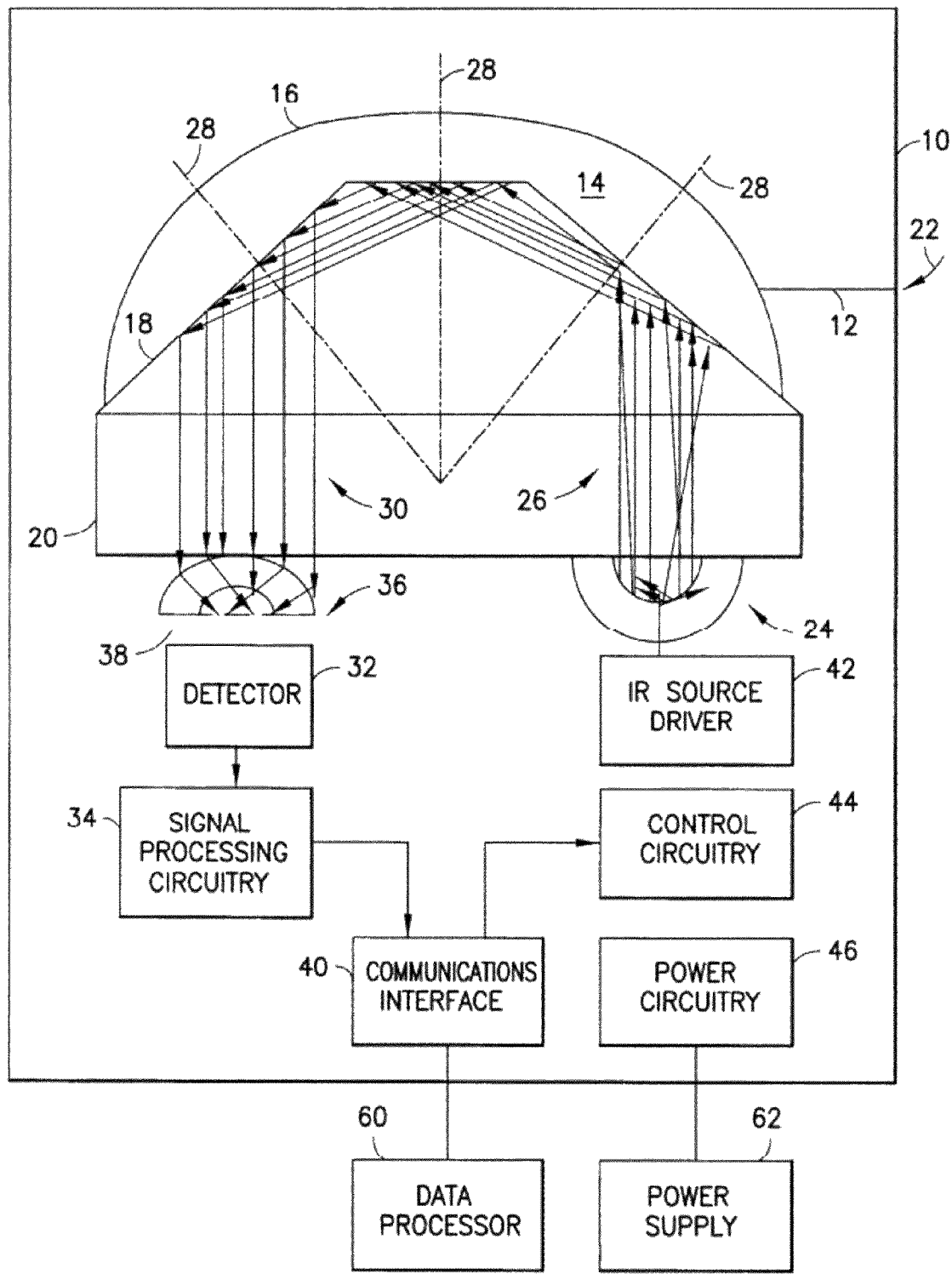
FIG. 1 is a schematic diagram of a carbon dioxide sensing apparatus in accordance with the present invention.

Turning now to FIG. 1, a carbon dioxide measuring apparatus 10 according to the invention includes a flowline 12 in fluid communication with a sample chamber 14, which is bounded by a cover 16 and an exterior surface 18 of an optically dense crystal 20. The flowline 12 provides for supply of a fluid sample (denoted by arrow 22) into the sample chamber 14. The apparatus 10 is particularly adapted for measuring carbon dioxide content of fluid samples 22 in which carbon dioxide is dissolved is an aqueous liquid solution (such as brine). More specifically, the fluid sample 22 fills the chamber 14 such that liquid fluid of the sample 22 is placed in direct contact with the exterior surface 18 of the crystal 20. An infrared light source 24 generates a beam of infrared radiation 26 that is directed into the crystal 20 such that it is incident on the interface of the crystal 20 and the liquid fluid of sample 22 at an angle larger than the critical angle $\theta_c$ measured with respect to the normal at the refractive boundary of the crystal 20, which is shown as line 28 in FIG. 1. The critical angle $\theta_c$ is a function of the refractive indices of both the sample and the crystal 20 and is given by:

$$\theta_c = \sin^{-1}\left(\frac{n_2}{n_1}\right). \tag{1}$$

Here, $n_1$ is the refractive index of the crystal 20 and $n_2$ is the refractive index of the sample 22. Above the critical angle of incidence, the beam 26 will be totally internally reflected at the interface of the crystal 20 and the liquid fluid of the sample 26. The internal reflection of the beam 22 can occur multiple times along the interface of the crystal 20 and the sample 22. The crystal 20 is typically realized from a high refractive index material (such as sapphire or diamond) in order to minimize the critical angle.

An important side effect of such total internal reflection is the propagation of an evanescent wave across the interface between the crystal 20 and the sample 22. Essentially, even though the entire incident wave is reflected back into the crystal 20, there is some penetration into the sample 22 at the interface. The evanescent wave propagates into the sample 22 at a depth (typically referred to as "penetration depth") that is a function of the wavelength and the refractive indices of both the sample and the crystal as given by:

$$D_p = \frac{\lambda}{2\pi n_1 \sqrt{\sin^2\theta - (n_2/n_1)^2}}. \tag{2}$$

This penetration depth is typically only a few microns (e.g. 0.5-10 μm).

In the regions of the infrared spectrum where the sample absorbs energy, the evanescent wave will be attenuated. The crystal 20 directs the reflected beam 30 (including the attenuated energy from each evanescent wave) for supply to an IR detector 32. Signal processing circuitry 34 (e.g. amplifier and filter circuitry, and A/D conversion circuitry) processes the output of the IR detector 32 to measure the intensity of the detected light within predetermined IR measurement bands as a function of time and generate digital data corresponding to such measurements. In the preferred embodiment, the predetermined IR measurement bands include a predetermined absorption band centered around 4.27 μm (e.g. 4.27 μm±75 nm), a predetermined reference band centered around 4 μm (e.g. 4 μm±75 nm or 5 μm±75 nm), and optionally an additional reference band centered around 3 μm (e.g. 3 μm±75 nm).

In the preferred embodiment, the reflected beam 30 (including the attenuated evanescent waves) is guided by a lens 36 through an optical filter 38 to the IR detector 32. The optical filter 38 provides bandpass optical filtering for the predetermined infrared measurement bands (e.g. the predetermined absorption band, the predetermined reference band, and possibly the additional reference band). The IR detector 32 includes an array of IR detector elements corresponding to the predetermined infrared measurement bands. The IR detector elements can employ material that is heated by absorbed IR energy (such as a thermopile or bolometer), pyroelectric material that changes surface charge in response to received radiation (such as lithium tantalate), or material that releases electric charges in response to incident radiation (such as lead selenide photonic detectors). Alternatively, a single IR detector element can be used. In this configuration, the optical filter can be mounted on a platform (e.g., filter wheel) that is moveable relative to the IR detector element to provide detection of the received IR signals in the respective bands.

The apparatus 10 further includes supporting electronics including a data communication interface 40, IR source driver circuitry 42, control circuitry 44, and power circuitry 46. The data communications interface 40 is electrically coupled to the signal processing circuitry 34 and operates to communicate the digital data generated by the signal processing circuitry 34 (which represents the intensity of the detected light within the predetermined IR measurement bands as a function of time) to an external data processor 60 (e.g., CPU) for storage and processing thereon. The data processor 60 processes the digital data supplied by the apparatus 10 to determine a concentration of carbon dioxide in the fluid sample 22 as described below in more detail. The IR source driver circuitry 42 generates electrical signals for supply to the IR light source 24 in order to operate the IR light source 24 as desired. The control circuitry 44 controls operation of the electrical, optoelectrical and/or optical elements of the apparatus 10 preferably in accordance with commands communicated from the external data processor 60 to the control circuitry 44 via the communications interface 40. For example, the control circuitry 44 can interface to the IR source driver circuitry 42 to activate and possibly control the operational mode of the IR light source 24 via commands issued by the external data processor 60 and communicated thereto via the communications interface 40. The control circuitry 44 can carry out other control operations as desired. The power circuitry 46 receives power supply signals from an external power supply 62 and transforms and/or conditions these signals into a form suitable for supply to the electrical and optoelectrical elements of the apparatus 10. The operation of the power circuitry 46 can include AC-DC conversion functions, DC-DC conversion functions, voltage regulation functions, current limiting functions, and other power conditioning functions, well known in the electrical arts.

Figure 2A:
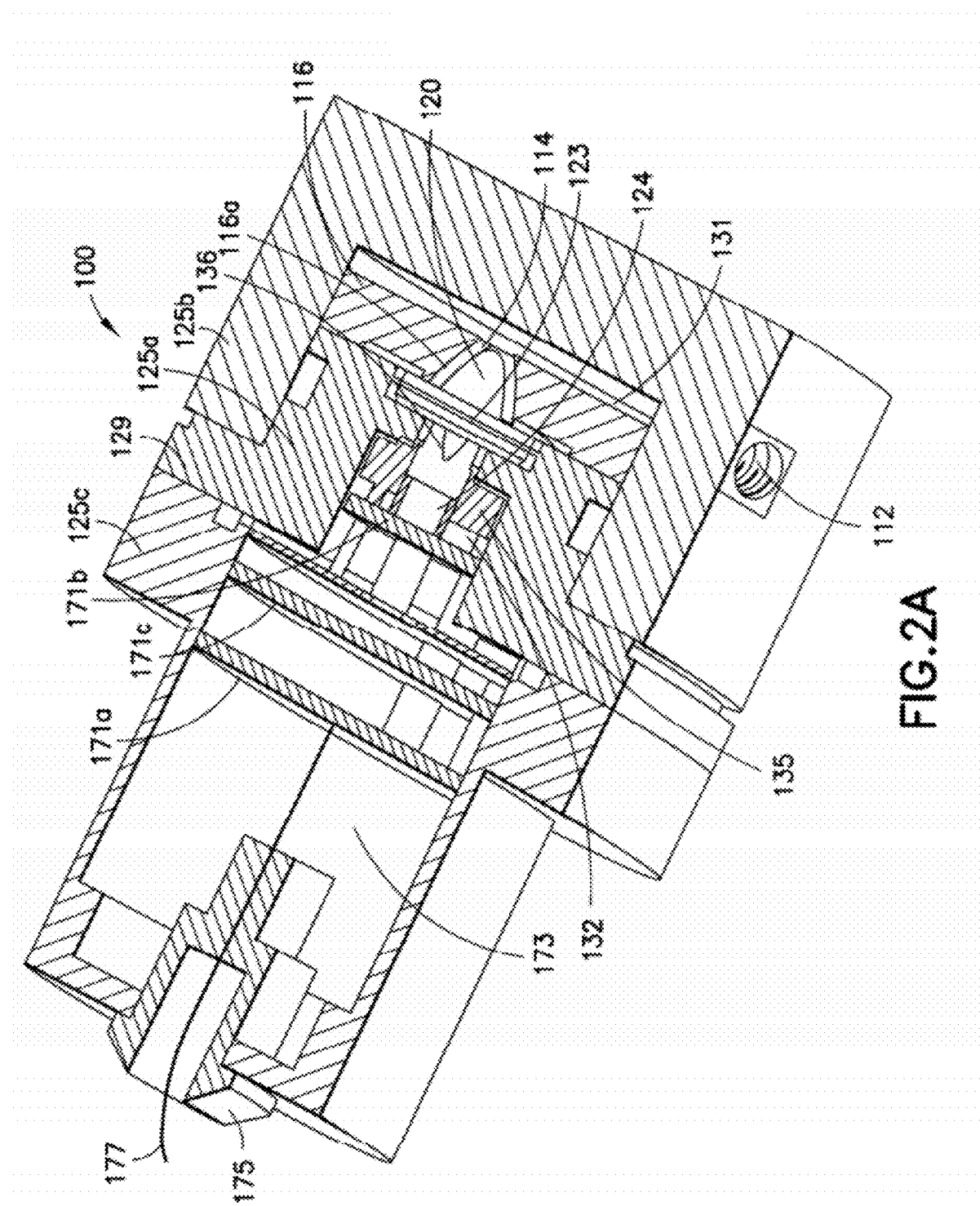
FIG. 2A is a cross-sectional view of an exemplary embodiment of a carbon dioxide sensor according to the present invention.
Figure 2B:
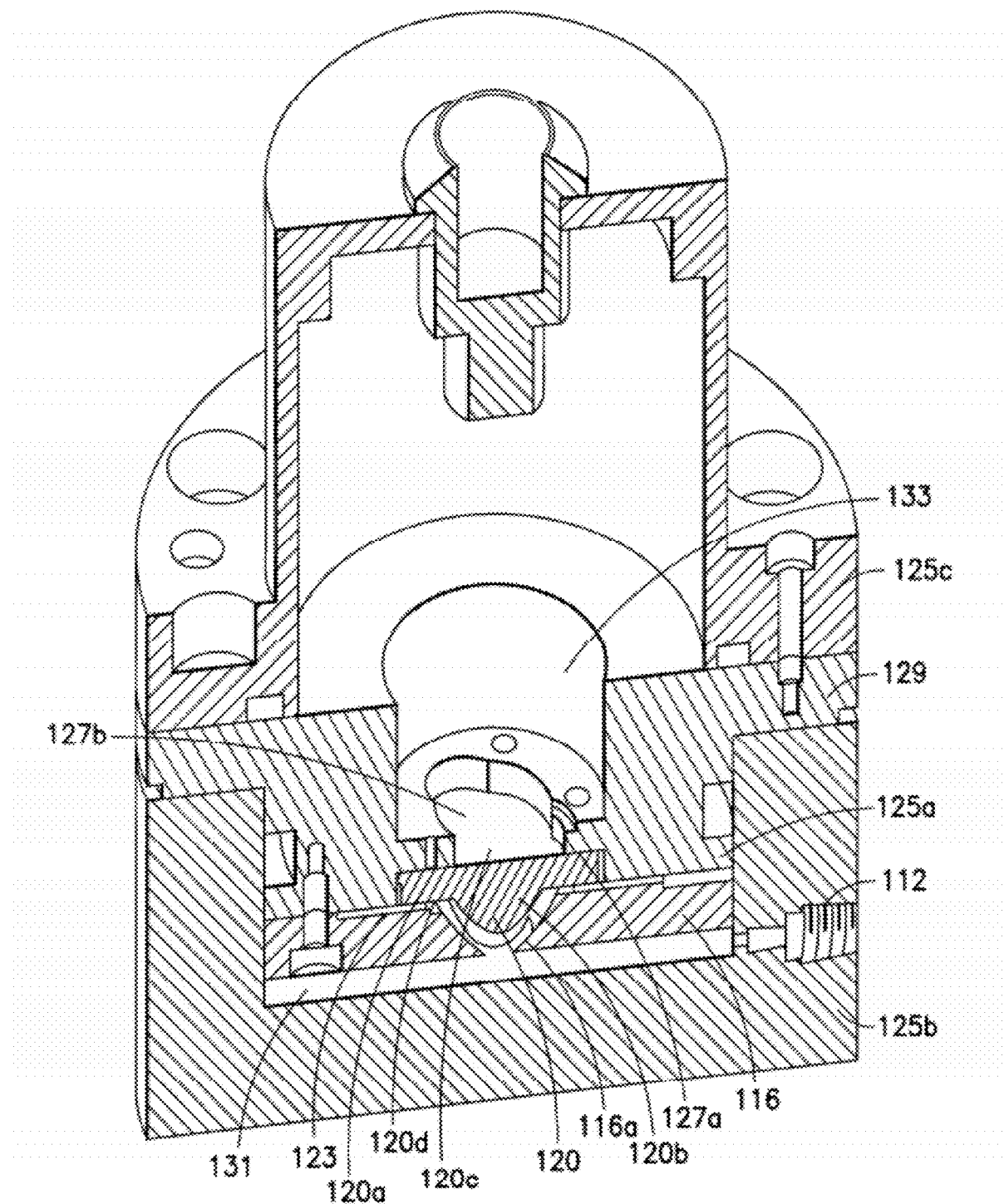
FIG. 2B is a partial cross-sectional view of the carbon dioxide sensor of FIG. 2A.

For downhole applications, the sensing crystal needs to be exposed to a high-pressure fluid, whereas the rest of the system such as the infrared source, the detectors, and the electronics need to be isolated from the fluid. FIGS. 2A and 2B illustrate an exemplary embodiment of a carbon dioxide measurement apparatus 100 in accordance with the present invention. The apparatus 100 includes an architecture similar to the apparatus 10 described above with respect to FIG. 1. More specifically, the apparatus 100 employs an optical assembly including a sapphire crystal 120 mounted between a surrounding housing part 125a (preferably realized from stainless steel) and a cover 116. As best shown in FIG. 2B, the crystal 120 has a base section 120a and a non-planar trapezoidal section 120b. The bottom surface 120c of the base section 120a of the crystal 120 is supported by a ledge 127a of the housing part 125a. A polymeric washer 123 (preferably realized from polyether ether ketone (PEEK)) is disposed between the top surface 120d of the base section 102a of the crystal 120 and the cover 116 to provide a seal between the cover 116 and the crystal 120. The cover 116 defines a diverging throughbore 116a that is shaped to accommodate the trapezoidal contour of the trapezoidal section 120b of the crystal 120 with a small gap there between. In accordance with one embodiment the gap may be 0.3 cm while the practical range of gap maybe between 0.03 to 0.5 cm. The ledge 127a of the housing part 125a defines a central opening 127b that exposes the bottom surface 120c of the base section 120a of the crystal 120. The housing portion 125a includes a flange section 129 that is disposed between and mated to two opposed housing parts 125b and 125c (which are preferably realized from stainless steel). In the preferred embodiment, the housing parts 125a, 125b and 125c provide sufficient structural integrity in high pressure environments (most preferably for environments that experience pressures up to 50 MPa).

The housing part 125b surrounds much of the optical assembly and defines a chamber 131 that is in fluid communication with both the diverging throughbore 116a of the cover 116 and a flowline port 112. Fluid samples to be measured are supplied under pressure to the chamber 131 via the flowline port 112 such that the fluid sample substantially fills the chamber 131 and the diverging throughbore 116a of the cover 116. In this configuration, the throughbore 116a provides a sample chamber 114 such that liquid fluid of the sample is placed in direct contact with the exterior surface of the crystal 120. In the preferred embodiment, the sensor apparatus is oriented during use such that the chamber 131 is disposed atop the throughbore 116a. This configuration ensures that gravity causes the liquid fluid to entirely fill the throughbore 116a (sample chamber 114) and if necessary allows for sufficient headspace in the chamber 131 to accommodate pressure change in a closed system.

The housing parts 125a and 125c support optoelectronics functionality that includes a broadband IR light source 124, a focusing lens 136, an optical filter array (not shown), an infrared detector array 132, and support-electronics (not shown). More specifically, the broadband IR light source 124 is supported in a central cavity 133 defined by the housing part 125a below the central opening 127b. The broadband IR light source 124 generates a broadband beam of infrared radiation that is directed into the crystal 120 such that it is incident on the interface of the crystal 120 and the liquid fluid of sample at a fixed angle larger than the critical angle $\theta_c$ measured with respect to the normal at the refractive boundary of the crystal 120 (FIG. 1). The broadband beam emitted by the broadband IR light source 124 contains energy over a broad range of the infrared frequency spectrum, including infrared radiation in the predetermined absorption band (e.g., 4.27 μm±75 nm) as well as in a predetermined reference band (e.g. 4.00 μm±75 nm or 5 μm±75 nm). The broadband beam emitted by the broadband IR light source 124 can also contain infrared radiation in an additional reference band (e.g., 3.00 μm±75 nm). The broadband IR light source 124 is preferably operated in a pulse mode. In the preferred embodiment, the broadband IR light source 124 is realized by a resistive heating element integrated onto a thin dielectric membrane which is suspended on a micro-machined silicon structure, such as the MIRL 17-900 marketed by Intex, Tucson, Ariz. A parabolic reflector (or other suitable collimator) collimates the IR light generated by the light-emitting element into an IR beam for output to the crystal.

In the preferred embodiment, the broadband IR light source 124 generates an IR beam with a fixed incident angle on the interface of the crystal 120 and the liquid fluid of sample over the operating range of temperature and pressure of the apparatus. For example, with a sapphire crystal 120 ($n_1$=1.654) in contact with an aqueous solution sample ($n_2$=1.33) together with an angle of incidence of θ=60° (which is greater than the critical angle $\theta_c$ of 53.5°), the penetration depth $D_p$ as a function of wavelength λ is given by the relation $D_p/\lambda$=0.3, so that at 4.27 μm, $D_p$=1.28 μm. In another example, with a diamond crystal 120 ($n_1$=2.43) in contact with an aqueous solution sample ($n_2$=1.33) together with an angle of incidence of θ=45° (which is greater than the critical angle θ, of 33.2°), the penetration depth $D_p$ as a function of wavelength λ is given by the relation $D_p/\lambda$=0.15, so that at 4.27 μm, $D_p$=0.64 μm. These configurations are suitable because the refractive index, of the aqueous liquid solution sample (e.g. brine) is not expected to change significantly over the operating range of temperature and pressure of the apparatus. This is also aided by the fact that the solubility of carbon dioxide in the aqueous liquid solution does not significantly change the density of the aqueous liquid solution. More specifically, the change in the refractive index due to dissolved carbon dioxide is a higher order correction and is not relevant for measuring dissolved carbon dioxide in the aqueous liquid solution to a reasonable level of accuracy.

Similar to the optical configuration shown in FIG. 1, the beam produced by the broadband IR light source 124 of FIGS. 2A and 2B is directed into the crystal 120 such that it undergoes a sequence of three reflections at the interface of the top surface of the crystal 120 and the fluid sample. The first reflection occurs along one angled top surface of the trapezoidal section 120b. The second reflection occurs along the flat top surface of the trapezoidal section 120b. And the third reflection occurs along the opposed angled top surface of the trapezoidal section 120b. After the third reflection, a focusing lens 136 directs the IR beam to the infrared detector array 132 through an optical filter array (not shown). A heat sink 135, preferably realized from anodized aluminum, is mounted with the cavity 133, and surrounds the infrared detector array 132. The heat sink 135 is thermally coupled to the infrared detector array 132 and operates to transfer heat away from the infrared detector array 132. In the preferred embodiment, the heat sink allows the infrared detector array 132 to function properly in high temperature environments (most preferably in environments that experience temperatures up to 100° C.). Thermoelectric cooling and/or passive cooling of the infrared detector array 132 can also be used if desired. The central cavity 173 defined by the housing parts 125a, 125b and 125c is filled with a chemically inert gas (such as nitrogen, argon or helium) at atmospheric pressure and hermetically sealed from the external environment by a plug 175. The chemically inert gas surrounds the infrared detector array 132 and ensures that $CO_2$ and water vapor are not present in the optical path of the sensor where they may give rise to erroneous absorption. Also, it prevents the electronic components from being oxidized.

The optical filter array (not shown) provides bandpass optical filtering for the predetermined infrared measurement bands, including the predetermined absorption band (e.g. 4.27 μm±75 nm), the predetermined reference band (e.g. 4.00 μm±75 nm, or 5 μm±75 nm) and optionally the additional reference band (e.g. 3.00 μm±75 nm). The IR detector array 132 includes a plurality of IR detector elements corresponding to the filter bands. The IR detector elements can employ material that is heated by absorbed IR energy (such as a thermopile or bolometer), pyroelectric material that changes surface charge in response to received radiation (such as lithium tantalate), or material that releases electric charges in response to incident radiation (such as lead selenide photonic detectors). Alternatively, a single IR detector element may be used. In this configuration, the optical filter array can be mounted on a platform (e.g. filter wheel) that is moveable relative to the single IR detector element to provide detection of the received IR signals in the respective bands. Other suitable IR filtering and detection arrangements can also be used.

The support electronics (not shown) are supported on three printed circuit boards 171a, 171b, and 171c mounted within the housing parts 125a and 125c. The support electronics include a data communication interface, IR source driver circuitry, control circuitry, and power circuitry, all of which carry out electrical and optoelectronic functions as described above with respect to the corresponding elements of FIG. 1. Wired conductors 177 carry communication signals that support data communication between the external data processor 60 and the support electronics as well as supply power signals to the support electronics.

In the preferred embodiment, the predetermined absorption band measured by the apparatus 10 (or 100) as described above is centered at 4.27 μm and has a bandwidth of 150 nm (e.g. 4.27 μm±75 nm). This particular absorption band is selected to maximize the absorption intensity of carbon dioxide while minimizing the absorption intensity of water and any potential interference resulting therefrom. Moreover, the predetermined reference band measured by the apparatus 10 (or 100) as described above is centered at 4.00 μm and has a bandwidth of 150 nm (e.g. 4.00 μm±75 nm). This particular reference band is selected where there is minimal absorption from carbon dioxide. The reference band can also be chosen to give minimal absorption of water. The predetermined absorption band and predetermined reference band are illustrated in FIG. 3, which show the absorption spectra lines of carbon dioxide (in gray) and water (in black) for the spectra range between 1 and 5 μm.

FIG. 3 shows intense absorption bands of carbon dioxide at 4.27 μm. These absorption bands originate from the fundamental, asymmetrical vibration (also called the asymmetrical stretch mode) along the molecular axis, relative to the mass center of the atoms. FIG. 3 also shows minimal absorption bands of water at 4.27 μm. In this manner, the predetermined absorption band centered at 4.27 μm maximizes the absorption intensity of carbon dioxide, and minimizes the absorption intensity of water and any potential interference resulting therefrom.

FIG. 3 also shows minimal absorption bands of both carbon dioxide and water at 4.00 μm. In this manner, the predetermined reference band centered at 4.00 μm has minimal absorption of both carbon dioxide and water. It is noted that 5.00 μm also has minimal absorption of both carbon dioxide and water, and thus can also be selected as part of the reference band. It is also noted that water does absorb a small amount of infrared radiation in the reference band centered at 4.00 μm as shown in the absorbance-wavelength plot for water of FIG. 4. Water exhibits similar absorption in the reference band centered at 5.00 μm.

The dissolution of carbon dioxide in water involves a sequence of reactions described by standard principles of chemical equilibria and dissociation constants under standard conditions (these are given for 25° C., 1 atm here) as shown below. These start with $CO_2$ dissolving into water to form molecular $CO_2$ in the liquid phase, which subsequently forms the carbonic acid molecule.

$$CO_2(aq) + H_2O \leftrightarrows H_2CO_3 \quad pK_{a1}=3.69 \qquad (3a)$$

$$H_2CO_3 + H_2O \leftrightarrows H_3O^+ + HCO_3^- \quad pK_{a2}=6.38 \qquad (3b)$$

$$HCO_3^- + H_2O \leftrightarrows H_3O^+ + CO_3^{2-} \quad pK_{a3}=10.32 \qquad (3c)$$

Among the total of four potential carbon-containing species (i.e., $CO_2$, $H_2CO_3$, $HCO_3^-$, $CO_3^{2-}$), only carbon dioxide ($CO_2$) exhibits its characteristic absorption in the specific spectra range around 4.27 μm. Molecular carbonic acid ($H_2CO_3$) exhibits its characteristic absorption in the specific spectra range around 6.6 μm. The bicarbonate anion ($HCO_3^-$) exhibits its characteristic absorption in the specific spectra range around 7.5 μm, while the carbonate anion ($CO_3^{2-}$) exhibits its characteristic absorption in the specific spectra range around 11.5 μm. It is noted that the spectral ranges of the molecular carbonic acid species ($H_2CO_3$), the bicarbonate anion species ($HCO_3^-$), and the carbonate anion species ($CO_3^{2-}$) are far removed from the spectra range around 4.27 μm for the dissolved carbon dioxide. Furthermore, their concentrations in relation to molecular $CO_2$ is small. This also means that knowing the amount of molecular $CO_2$ in the liquid phase is almost the same as the knowing the total $CO_2$ dissolved.

In order to characterize the concentration of carbon dioxide dissolved in the aqueous fluid sample acquired by the apparatus 10 or 100 as described above, the data processor 60 employs a response model that relates such carbon dioxide concentration to the spectral intensity data for the predetermined absorption band and the predetermined reference band acquired and output by the apparatus 10 (or 100). More specifically, the concentration of carbon dioxide dissolved in an aqueous solution in contact with the internal reflection crystal (20, 120) as described herein can be determined by the intensity $I(\lambda, T)$ of the infrared radiation at a particular wavelength $\lambda$ as measured by the infrared detector (32 or 132) at a given temperature T. The absorbance (or optical density) A is related to the intensity $I(\lambda, T)$ as follows:

$$A(\lambda, T) = -\ln\left(\frac{I(\lambda, T)}{I_0(\lambda, T)}\right) \quad (4)$$

where $I_o(\lambda,T)$ is the measured reference intensity at the same wavelength but in the absence of any absorbing sample.

The absorbance $A(\lambda,T)$ is also related to the molar concentrations of the components of the aqueous solution of the sample and the optical path length L by the Beer-Lambert law:

$$A(\lambda,T) = \Sigma \in_i(\lambda,T) C_i L \quad (5)$$

where $\in_i (\lambda,T)$ is the absorption coefficient of the component i at a particular wavelength $\lambda$ and $C_i$ is the molar concentration of the respective component. The sum is over all species i.

Based on the relationships of Eqs. (4) and (5) and an assumption that the aqueous solution is a carbon dioxide-water binary system, the absorbance of the sample is related to the absorbance of the carbon dioxide component and water component of the sample for a wavelength in the predetermined absorption band (i.e., $\lambda_2 = 4.27$ μm) as follows:

$$A(\lambda_2, T) = -\ln\left(\frac{I(\lambda_2, T)}{I_0(\lambda_2, T)}\right) = \varepsilon_C(\lambda_2, T) C_C L + \varepsilon_w(\lambda_2) C_w L \quad (6)$$

where $\in_C (\lambda_2)$ is the absorption coefficient of the carbon dioxide component of the sample at the particular wavelength $\lambda_2$ and $C_C$ is the molar concentration of the carbon dioxide component of the sample, and $\in_w (\lambda_2)$ is the absorption coefficient of the water component of the sample at the particular wavelength $\lambda_2$ and $C_w$ is the molar concentration of the water component of the sample.

Assuming that the concentration of carbon dioxide has a negligible affect on water concentration, the absorbance of the water component of the sample can be considered a fixed value $\beta$. As shown subsequently, this assumption allows Eqn. (6) to be rewritten as follows:

$$-\ln\left(\frac{I(\lambda_2, T)}{I_0(\lambda_2, T)}\right) = \quad (7)$$

$$-\ln\left(\frac{I(\lambda_2, T)}{k_2(T) I_0(\lambda_1, T)}\right) = -\ln\left(\frac{I(\lambda_2, T)}{k_3(T) I(\lambda_1, T)}\right) = \alpha(T) C_C + \gamma(T)$$

$\alpha = \in_C(\lambda_2)L$, $k_2$, $k_3$ and $\gamma$ are temperature-dependents. As we shall see below this equation is difficult to implement with the first two ratios, when the source has a drift in the incident intensity. We prefer the third ratio that does not require $I_0$. The $-1$ $nk_3(T)$ may be absorbed in the calibration process into $\chi(T)$ and $\beta(T)$.

A calibration process may be used to solve for the two unknown functions of temperature $\alpha$ and $\gamma$ or $\gamma - \ln k_3$ of Eqn. (7). Once the calibration process is complete and the temperature dependent functions are known, the molar concentration of carbon dioxide in the sample ($C_c$) can be derived from the intensity $I(\lambda_2, T)$ (i.e., the intensity of the detected infrared radiation in the predetermined absorption band) and $I(\lambda_1,T)$ (i.e., the intensity of the detected infrared radiation in the predetermined reference band.

More specifically, the calibration process cycles over a sequence of temperature levels beginning at an elevated starting temperature and a lower ending temperature, in which carbon dioxide is dissolved at a known partial pressure. The elevated starting temperature and lower ending temperature preferably corresponds to the upper temperature limit and lower temperature limit, respectively, of the desired application. The downward sequencing of temperature assures that the carbon dioxide remains dissolved, provided the absolute pressure is not allowed to change to prevent exsolution (this may be done with an accumulator or bellows). For the elevated starting temperature, an equilibrated solution of carbon dioxide dissolved in water that has been heated to match the elevated starting temperature is introduced into the sample chamber of the apparatus, and the system is controlled to measure and record the intensities $I(\lambda_2,T)$ and $I(\lambda_1,T)$ for that particular temperature. The temperature of the equilibrated solution in the sample chamber of the apparatus is allowed to lower to the next temperature level in the sequence, and the system is controlled to measure and record the intensities $I(\lambda_2,T)$ and $I(\lambda_1,T)$ for that particular temperature. Such temperature monitoring and measurements are repeated for each temperature level in the sequence until the intensities for all temperature levels have been measured and recorded. The sequence of experiments may be repeated with different dissolved carbon dioxide concentration at the starting temperature by having a different equilibration partial pressure of carbon dioxide. One can then fit the data values for the natural log of the recorded intensities $-\ln(I(\lambda_2, T)/I(\lambda_1, T))$ to solve for the temperature dependent coefficients of Eq. 7. $\alpha(T)$ and $\gamma(T) - \ln k_3(T) = \beta(T)$ are then known.$\alpha\beta$ The theory illustrative of the principles is given below. The response model employs six intensity parameters where three intensity parameters are relevant to the predetermined absorption band (e.g., the band centered around 4.27 μm and three corresponding intensity parameters are relevant to the predetermined reference band (e.g., the band centered around 4.00∈μm). For the sake of description, the three intensity parameters that relate to the predetermined absorption band can be subscripted with a 2, and the three intensity parameters that relate to the predetermined reference band can be subscripted with a 1. Table 1 below shows these six intensity parameters.

TABLE 1

Definition of intensities used in response model to determine the concentration of dissolved carbon dioxide in brine water using a two channel infrared sensor apparatus

| Sample Formulation | Intensity in predetermined reference band ($\lambda_1$ = 4.00 µm) | Intensity in predetermined absorption band ($\lambda_2$ = 4.27 µm) |
|---|---|---|
| inert gas or vacuum | $I_{o1}$ | $I_{o2}$ |
| water | $I_{w1}$ | $I_{w2}$ |
| water + $CO_2$ | $I_{c1}$ | $I_{c2}$ |

The intensity parameters $I_{o1}$ and $I_{o2}$ are measured with the internal reflection crystal in contact with an inert gas (such as helium) or in a vacuum. $I_{o1}$ is measured for the wavelength $\lambda_1$, and $I_{o2}$ is measured for the wavelength $\lambda_2$. These intensities are a function of the output of the source at the two wavelengths and the attenuation in the optical path (e.g., transmission of filter, absorption and reflection losses by internal reflection crystal) and may change with temperature. The intensity parameters $I_{o1}$ and $I_{o2}$ may be measured before or after use but not during the use, i.e., with the crystal in direct contact with an aqueous solution (brine) with the solute carbon dioxide. Therefore the method we use must be preferably independent of the availability of these two measurements. The intensity parameters $I_{w1}$ and $I_{w2}$ are typically not measured, but can be derived from calibration parameters as described below. The intensity parameters $I_{c1}$ and $I_{c2}$ are measured during use, i.e., with the crystal in direct contact with an aqueous fluid sample (brine) having solute carbon dioxide. $I_{c1}$ is measured for the wavelength $\lambda_1$, and $I_{c2}$ is measured for the wavelength $\lambda_2$.

Figure 4:
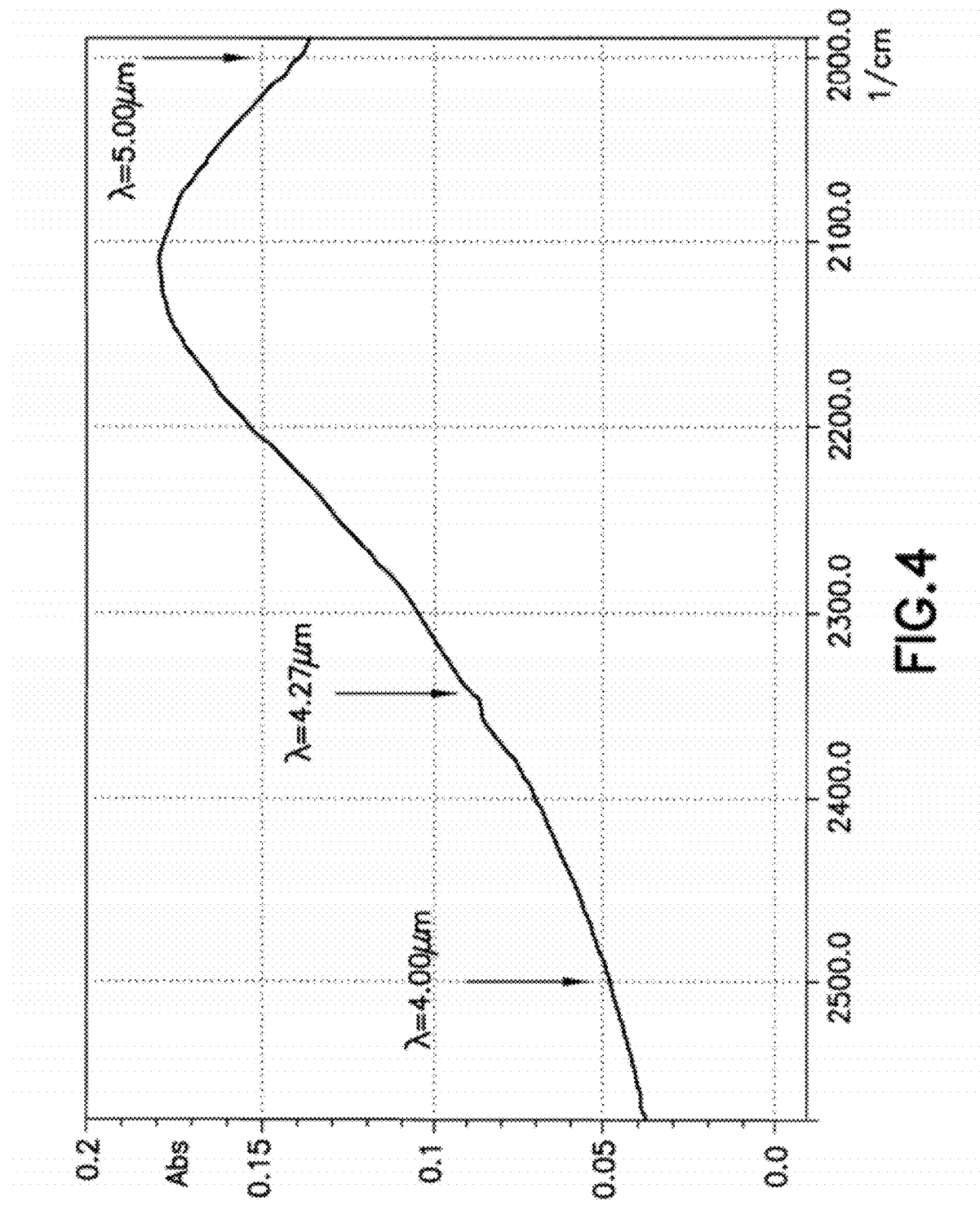
FIG. 4 is a graph of the absorption of water as a function of wavelength in the spectral range between 3.85 μm (2600 l/cm) and 5.00 μm (2000 l/cm) as measured by the exemplary sensor of FIGS. 2A and 2B at a temperature of 22° C.

The intensity parameter $I_{w1}$ can be related to the intensity parameter $I_{o1}$ by the relationship:

$$I_{w1} = k_1(T) I_{o1} \tag{8}$$

where $k_1$ is a temperature dependent parameter coefficient that depends on the absorption coefficient of water. This is equivalent to fixing the value of the absorbance $A_{w1}$ of pure water to the value of $-\ln k_1$ at a temperature of interest. FIG. 4 illustrates measurements of the absorbance $A_{w1}$ of pure water over a range of wavelengths at 22° C. In this example, the measured absorbance $A_{w1}$ at $\lambda_i$=4.00 µm (2500 cm$^{-1}$) is 0.0047, and therefore $k_1$=0.9953. The parameter $k_1$ dependence on temperature is due to the infrared spectrum of water being a function of the temperature. The parameter $k_1$ can be determined at a series of temperatures by measuring $I_{o1}$ (absence of water) and $I_{w1}$ (presence of water), whereupon the functional dependence of $k_1$ on temperature can be obtained. As outlined before and shown further below, our calibration does not need a direct measurement of this parameter.

In the preferred embodiment, the predetermined reference band ($\lambda_1$) is selected such that the presence of dissolved carbon dioxide in the water of the sample has no effect on the intensity measured at the predetermined reference band ($\lambda_1$). In this case, the intensity parameter $I_{c1}$ is equal to the intensity parameter $I_{w1}$ and therefore $$I_{c1} = I_{w1} = k_1(T) I_{o1}. \tag{9}$$

For the predetermined absorption band ($\lambda_2$), the intensity parameter $I_{o2}$ can be related to the intensity parameter $I_{o1}$ by the relationship:

$$I_{o2} = k_2(T) I_{o1}. \tag{10}$$

The parameter $k_2$ is not expected to have a large dependence on temperature. The dependence arises from the transmissivities of the optical filters and the responses of the infrared detectors for the predetermined reference band ($\lambda_1$) and the predetermined absorption band ($\lambda_2$) having different temperature coefficients.

Eq. (10) may be combined with Eq. (8) as follows:

$$I_{o2} = \frac{k_2(T)}{k_1(T)} I_{w1} = k_3(T) I_{w1} = k_3(T) I_{c1}, \tag{11}$$

where $$k_3(T) = \frac{k_2(T)}{k_1(T)}.$$

According to Eqn. (6), the absorbance $A_{c2}$ of the aqueous solution fluid sample for the predetermined absorption band ($\lambda_2$) is given by:

$$A_{c2} = -\ln\left(\frac{I_{c2}}{I_{o2}}\right). \tag{12}$$

Eqn. (12) can be rewritten by combining with Eqn. (11) as follow:

$$A_{c2} = -\ln\left(\frac{I_{c2}}{k_3(T) I_{c1}}\right) = -\ln\left(\frac{I_{c2}}{k_3(T) I_{w1}}\right) \tag{13}$$

Based on an assumption that the aqueous solution of the fluid sample is a carbon dioxide-water binary system, the absorbance $A_{c2}$ of the fluid sample consists of a fixed contribution from the water component (denoted $A_{w2}$) and a variable contribution from the dissolved carbon dioxide (denoted $\Delta A$) as given by:

$$\Delta A = A_{c2} - A_{w2} \tag{14}$$

which under the conditions of interest will change linearly with the dissolved concentration of carbon dioxide. We neglect the small changes in the water signal due to the small changes in the concentration of water with the dissolved carbon dioxide.

According to Eq. (6), $A_{w2}$ is given by:

$$A_{w2} = -\ln\left(\frac{I_{w2}}{I_{o2}}\right). \tag{15}$$

Eq. (15) can be rewritten by combining with Eq. (11) as follows:

$$A_{w2} = -\ln\left(\frac{I_{w2}}{k_3(T) I_{c1}}\right). \tag{16}$$

The parameter $I_{w2}$ can be measured from the output of the sensor apparatus when the crystal is in direct contact with water only, which is not feasible, $I_{w2}$ with the relationship of the form:

$$I_{w2} = k_4(T) I_{w1} = k_4(T) I_{c1} \tag{17}$$

where $k_4$ is a temperature dependent parameter that describes the relationship between the absorption due to water at the two wavelengths under consideration.

Eq. (16) can be rewritten by combining with Eq. (17) as follows:

$$A_{w2} = -\ln\frac{k_4(T)I_{c1}}{k_3(T)I_{c1}} = -\ln\left(\frac{k_4(T)}{k_3(T)}\right) = k_5(T) \quad (18)$$

where $k_5(T)$ is a temperature dependent parameter.

The parameter $k_5(T)$ is fixed for a given temperature. For example, in the spectrum of FIG. 4, the measured absorbance $A_{w2}$ of pure water at $\lambda_2 = 4.27$ μm (2342 cm$^{-1}$) is 0.088, and therefore $k_5 = 0.088$ and $k_4/k_3 = 0.9158$. In general, the parameter $k_5$ is expected to be a function of temperature since the infrared spectrum of water is a function of the temperature at which it is collected.

Eq. (14) can be rewritten by combining with Eqs. (13) and (18) as follows:

$$\Delta A = A_{c2} - A_{w2} = -\ln\left(\frac{I_{c2}}{k_3(T)I_{c1}}\right) - k_5(T). \quad (19)$$

Assuming that the Beer-Lambert law applies, and that the increase in absorbance at $\lambda_2$ is proportional to carbon dioxide concentration, at the low solute concentration levels, Eq. (19) can be written as:

$$\Delta A = -\ln\left(\frac{I_{c2}}{k_3(T)I_{c1}}\right) - k_5(T) = k_6(T)C_c, \quad (20)$$

where $k_6$ is a temperature-dependent coefficient, and $C_c$ is the molar concentration of dissolved carbon dioxide in the sampled fluid.

Eq. (20) can be expressed in the form:

$$\ln\left(\frac{I_{c2}}{I_{c1}}\right) = k_6(T)C_c + \ln k_3(T) - k_5(T) = \alpha(T)C_c + \beta(T) \quad (21)$$

where $\alpha(T) = k_6(T)$ and $\beta(T) = \ln k_3(T) - k_5(T)$ Eq. (21) Eq. (7). Calibration can be performed by determining the parameters over a range of temperatures and applied gas pressures so that $\alpha$ and $\beta$ are determinable functions of temperature. This avoids having to measure all of the k constants independently.

For completeness, it is useful to know that the parameter $k_1(T)$ is related to the absorbance of water in the predetermined reference band ($\lambda_1 = 4.00$ μm) and can be determined by $$-\ln\left(\frac{I(\lambda_1, T)}{I_{o1}}\right)$$

with the crystal in contact with of a pure water at various temperatures. The intensity $I_{o1}$ parameter is expected to be a function of temperature as the transmission of the reference filter and the performance of the detector (including associated electronics) are dependent on the temperature. $I(\lambda_1, T)$ can be equated to the intensities $I_{w1}$ or $I_{c1}$ ($I(\lambda_1, T) = I_{w1} = I_{c1}$) and can be determined from the intensity measured at $\lambda_1$. The functionality of $k_1$ can be determined by measuring $L_i$ (absence of water) and $I_{w1}$ (presence of water) at various temperatures. $k_1$ The ratio $I_{o2}/I_{o1}$ or $k_2(T)$ can be determined by a measurement of $I_{o1}$ and $I_{o2}$ for an inert gas or in vacuum at the wavelengths $\lambda_1$ and $\lambda_2$, respectively at various temperatures, if necessary.

The ratio $I_{w2}/I_{w1} = I_{w2}/I_{c1}$ defines $k_4(T)$ and is equivalent to knowing the ratio of absorbance of water at $\lambda_1$ and $\lambda_2$. In general, $k_4$ is temperature dependent, but only to the extent of differences in the absorption spectrum of water at these wavelengths at different temperatures. By measuring $I_{o1}$ and $I_{o2}$ (absence of water) and $I_{w1}$ and $I_{w2}$ (presence of water) at various temperatures, we may quantify the functionality.

The parametric function $k_6(T)$ is essentially the absorption coefficient of carbon dioxide dissolved in water at the fixed optical path length of the penetration depth into water via evanescent wave. The parameter $k_6(T)$ is determined as described above for the determination of $\alpha(T)$.an The parametric function $\beta(T)$ may also be obtained from $k_5(T) - \ln k_3(T)$, rather than from the experimental procedure given before.

Figure 5A:
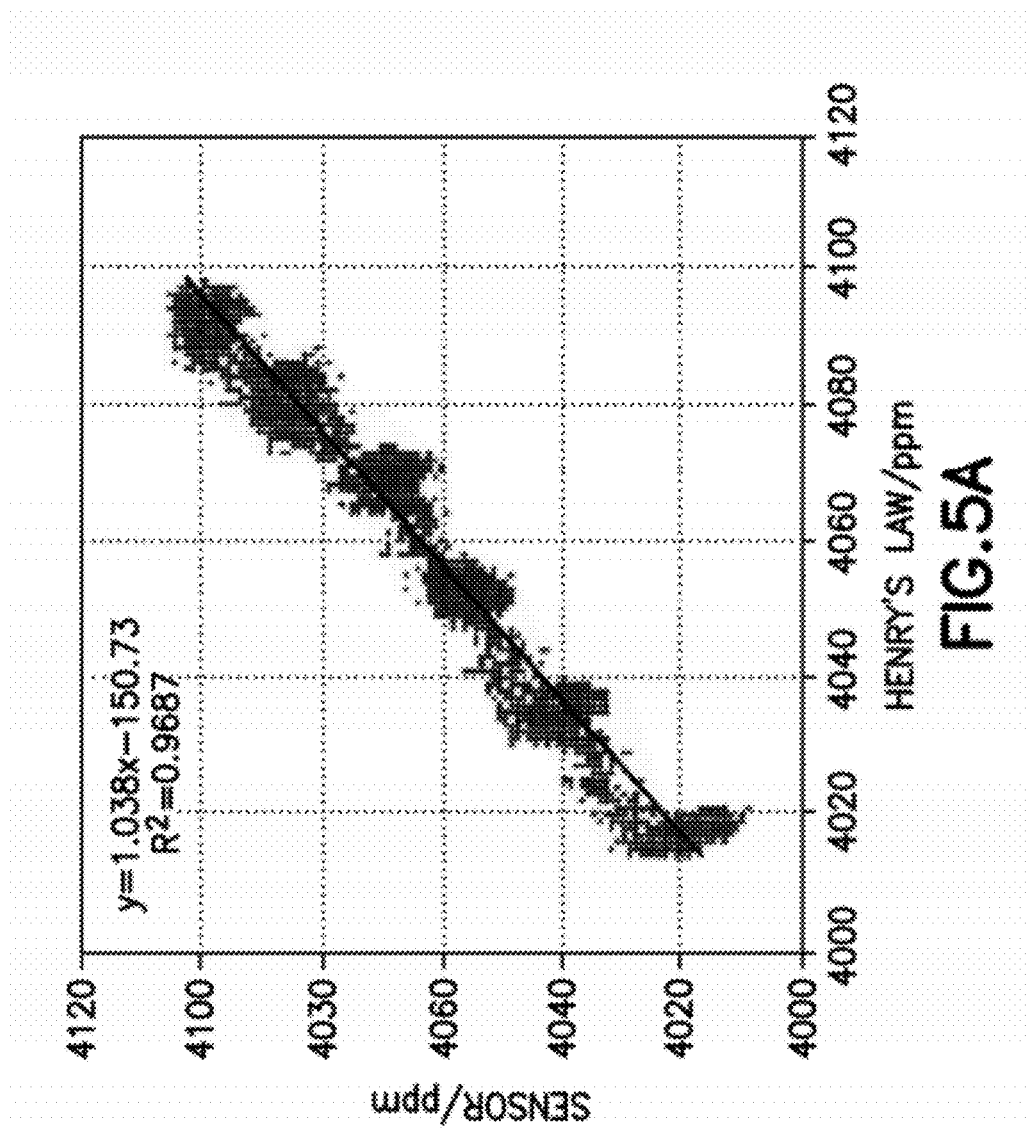
FIG. 5A is a graph of exemplary measurements of the concentration of carbon dioxide dissolved in water as measured by the exemplary sensor of FIGS. 2A and 2B relative to theoretical calculations based on Henry's law.
Figure 5B:
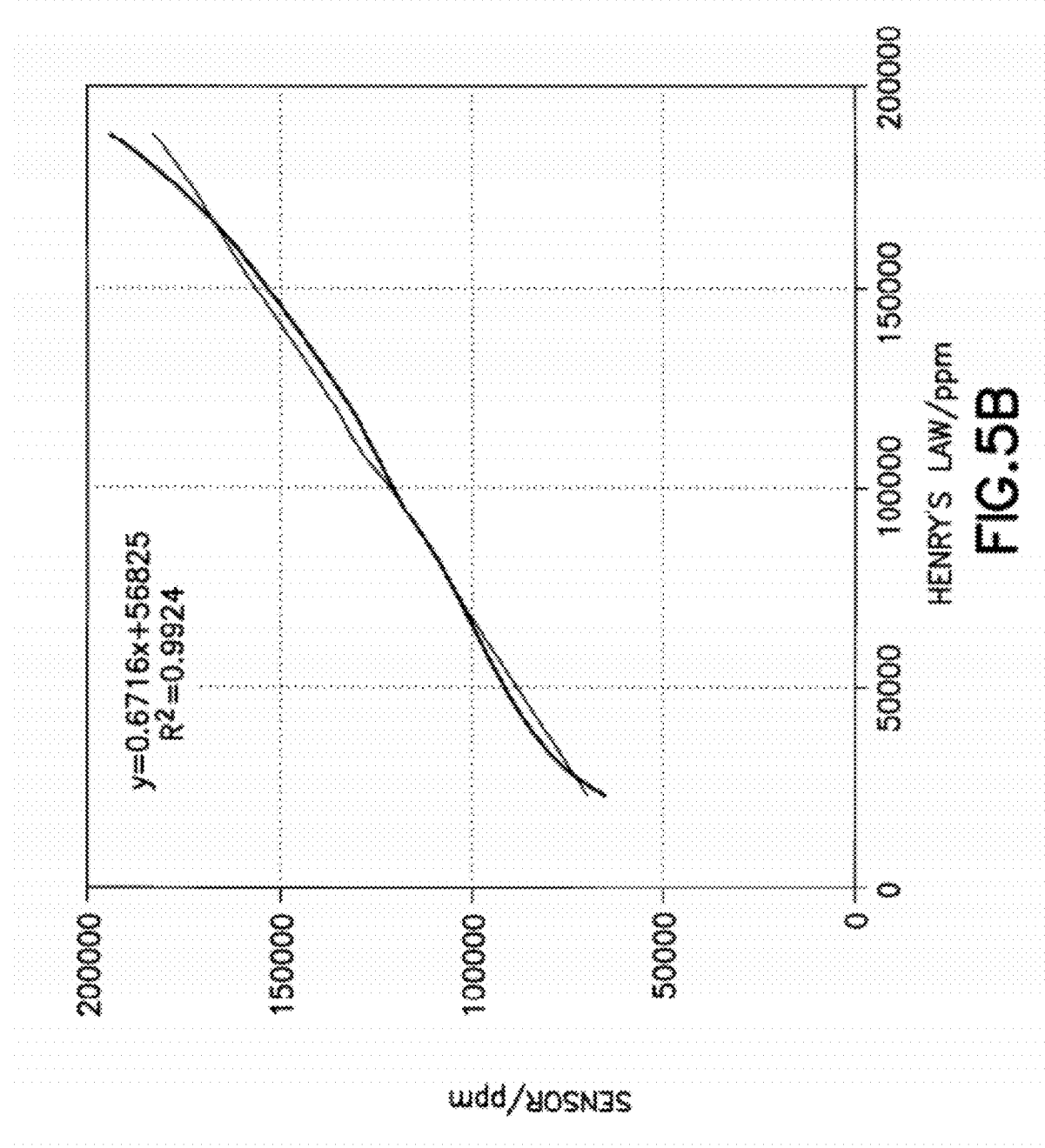
FIG. 5B is another graph of exemplary measurements of the concentration of carbon dioxide dissolved in water as measured by the exemplary sensor of FIGS. 2A and 2B relative to theoretical calculations based on Henry's law.

For small perturbations, a simple testing method is possible to verify the working of the sensor. The experiment is conducted above the critical temperature of carbon dioxide. A head-space of carbon dioxide in gas or supercritical state is provided. As long as the headspace is allowed to be present, the dissolved carbon dioxide is described by thermodynamic equilibrium at the measured pressure and temperature if one knows the vapor pressure of water (or neglects it, if it is small). FIGS. 5A and 5B illustrate measurements of the concentration of carbon dioxide dissolved in water as a result of a temperature perturbation. The measurements are acquired using the carbon dioxide measurement system as described above with respect to FIGS. 2A and 2B with the crystal 120 fully immersed in a fluid sample of carbon dioxide dissolved in water. A small headspace exists in the closed system allowing for pressure change, while allowing two-phase thermodynamic equilibrium. The tests of FIGS. 5A and 5B were initiated using a programmed temperature perturbation that, combined with the corresponding pressure change in the gas phase, leads to change of carbon dioxide concentration to reflect the new chemical equilibrium between the gas and liquid phases. The measurements were conducted in the absorption band centered around 4.27 μm as well as a reference band centered around 4.00 μm.

In the test of FIG. 5A, the temperature of the fluid sample was ramped down in five steps from 74° C. to 69° C. over a period of thirty-four hours, causing a corresponding pressure change from 77 psi to 73 psi. FIG. 5A shows that the measurements of the system exhibit excellent correlation to Henry's law.

In the test of FIG. 5B, the temperature of the fluid sample was ramped from 0° C. to 100° C. over a period of 13 hours, with a corresponding pressure from 83 psi to 4500 psi. Again, the measurements exhibit strong correlation to Henry's law. As understood by one skilled in the art, curve 5B shows the excellent matching between the measured $CO_2$ concentration to that predicated by Henry's law.

Henry's law states that at a constant temperature, the amount of a given gas dissolved in a given type and volume of liquid is directly proportional to the partial pressure of that gas in equilibrium with that liquid. The idealized form of Henry's law gives:

$$X_i = \frac{P_i}{H} \quad (22)$$

where $X_i$ is the mole fraction of carbon dioxide dissolved in liquid at an applied partial pressure $P_i$, and H is the Henry's law constant.

For example, as described by Carroll et al in *J. Phys. Chem. Ref Data*, 20, 1201-1209 (1991), for $P_i \leq 1$ MPa and temperature T in the range 273-433 K, H may be expressed as:

$$\text{Ln}H = -6.8346 + \frac{1.2817 \times 10^4}{T} - \frac{3.7668 \times 10^6}{T^2} + \frac{2.997 \times 10^8}{T^3} \quad (23)$$

In this manner, the temperature of the solution and the partial pressure of the carbon dioxide gas can be used to infer the dissolved carbon dioxide concentration. The inference is a good cross-check on the calibration. From these measurements, (22) and (23) can be used to derive the mole fraction of carbon dioxide dissolved in the liquid according to the ideal form of Henry's law. For dilute solutions, the concentration of carbon dioxide dissolved in water expressed in moles per liter of solution is given by $55.55X_i$. Alternatively, the concentration of carbon dioxide dissolved in water expressed in grams per liter of solution is given by $2444.4X_i$. At high values of $P_c$ when Henry's law is no longer adequate to calculate the solubility of carbon dioxide, a more elaborate equation of state is required. An example of such an equation of state is described in Duan, Z. and Sun, R., "An improved model calculating $CO_2$ solubility in pure water and aqueous NaCl solutions from 273 to 533 K and from 0 to 2000 bar," *Chem. Geol.*, 193, 257-271 (2003), herein incorporated by reference in its entirety.

The present invention as described above is adapted to measure the concentration of carbon dioxide dissolved in an aqueous solution. Specifically, the calibration process of the invention expects positive values of absorbance due to water at the predetermined absorption band and the predetermined reference band. In the event that water is not present in the fluid sample, errors will be introduced into the measurements carried out by sensing system. In order to deal with this issue, the apparatus can make an additional measurement in a reference band that will unequivocally indicate the presence of water. One possible wavelength is $\lambda_3 = 3.00$ μm (3340 cm$^{-1}$), which corresponds to the peak absorbance of the O—H stretching band. This is supported by the sensor apparatus described above (e.g., 3 μm±75 nm). The lack of water present in the fluid sample in contact with the ATR crystal would be indicated by a large rise in the measured intensity ($I(\lambda_3)$) in the additional reference band corresponding to a decrease in the absorption ($A(\lambda_3)$) in the additional reference band. This measurement can be used to selectively initiate the measurement of carbon dioxide concentration as described above, or to validate (or invalidate) the measurement of carbon dioxide concentration as described above. It can also be used as a gating mechanism to control the reporting of carbon dioxide concentration measurements to a user.

The present invention also utilizes a reference intensity $I_o$ where there is little or no absorption by the sample. In the preferred embodiment, this reference intensity is measured as a particular band (e.g., a band centered around 4.00 μm or 5.00 μm) that is part of the infrared beam directed into and exiting from the ATR crystal of the sensor apparatus. In an alternate configuration, the infrared source beam is split into two parts. One part is directed to the ATR crystal as described herein. The other part is directed to an IR detector element and records the measured intensity as the reference intensity $I_o$. In yet another configuration, a light detection element (e.g. a photodiode) and feedback circuitry can be used to measure the intensity of the infrared beam and maintain such intensity at a constant level (the reference intensity $I_o$) over the measurements carried out by the sensor apparatus.

The sensor apparatus as described herein can also be adapted to measure the concentration of other carbon-containing species related the dissolution of carbon dioxide in water. As outlined in Eqs. (3a)-(3c), these species include molecular carbonic acid ($H_2CO_3$), the bicarbonate anion ($HCO_3^-$), and the carbonate anion ($CO_3^{2-}$). Carbonic acid ($H_2CO_3$) exhibits its characteristic absorption in the specific spectra range around 6.6 μm. The bicarbonate anion ($HCO_3^-$) exhibits its characteristic absorption in the specific spectra range around 7.5 μm. The carbonate anion ($CO_3^{2-}$) exhibits its characteristic absorption in the specific spectra range around 11.5 μm. Such measurements can be performed with a suitable ATR crystal material together with optical filters that provide for narrow bandpass filtering in the spectra range for the respective species. The electronics of the system can be adapted to process data from these multiple channels in order to derive measures of the concentration of the carbon-containing species based upon the infra-red intensities measured by the apparatus. One ATR crystal that has suitable transmission properties in the spectral range 6-12 μm is diamond. The calibration procedure for the additional wavelengths is similar to that described above; for each additional measurement values of $I_{oi}$, $I_{wi}$ and $I_{ci}$ will be required at the specified wavelengths together with corresponding values of $k_i$.

The sensor apparatus as described herein can readily be adapted to measure the concentration of carbon dioxide in other liquid solutions such as a liquid hydrocarbon environment. In case of the solvent being liquid hydrocarbon, the intensities $I_{w1}$ and $I_{w2}$ are replaced by $I_{h1}$ and $I_{h2}$, and $I_{c1}$ and $I_{c2}$ would be measured for $CO_2$ dissolved in the hydrocarbon. Otherwise the calibration procedure is identical to that for water. However, the reference band to determine whether or not the ATR crystal is in contact with liquid hydrocarbon would be shifted to $\lambda = 3.45$ μm from the value of $\lambda = 3.00$ μm used for water.

According to one aspect of the invention, the sensor apparatus as described herein can be integrated as part of a downhole logging tool that is deployable within a subterranean wellbore. Examples of such wellbores include observation wells and injection wells that extend to a subterranean formation that is used for carbon dioxide sequestration, such as a saline aquifer or a depleted oil field. It can also be deployed in observation wells that do not extend down to the subterranean formation that is used for carbon dioxide sequestration (such as monitoring wells that are located above the subterranean formation used for carbon dioxide sequestration). The sensor apparatus as described herein can also be placed in permanent locations within the subterranean formation used for carbon dioxide sequestration in order to monitor the carbon dioxide concentration of the fluids therein. A number of sensor apparatus can be deployed at different depths and lateral spacing as needed.

FIGS. 6A and 6B show the sensor apparatus of the present invention as part of two commercially-available downhole logging tools. FIG. 6A shows the sensor apparatus attached to the flow-line of Schlumberger's modular formation dynamics tester tool or a cased hole dynamics tester (MDT™ or a CHDT™). The MDT or a CHDT employ a probe that is directly pressed to the reservoir with an elastomeric pad providing isolation between the probe and the borehole fluid. The CHDT includes additional provisions to drill a hole through the casing and seal the hole after the sampling test is conducted. In both of the tools, with a pressure drawdown, the formation fluid sample is acquired via the probe into the tool flow-line, passing the sensor apparatus of the present invention. After passing by the sensor, the fluid may be discarded to the borehole, or a dump chamber, or collected in a sample chamber. The tool includes a data processor and a telemetry bus (not shown). The data processor interfaces to the sensor to perform the data processing operations that determine the carbon dioxide concentration as a function of the infrared intensity measurements carried out by the sensor apparatus. The telemetry bus communicates data and control signals between the data processor and a surface-located system. Furthermore, the deployment of reference filters at both $k=3.00$ μm and $\lambda=3.45$ μm would ensure that the phase in which the concentration of carbon dioxide is being determined is known. To elaborate, the magnitude of the intensities at $\lambda=3.00$ μm and $\lambda=3.45$ μm would indicate whether the measurement was being made in water, hydrocarbon, or a mixture of hydrocarbon and water. The correct calibration algorithm may then be chosen. In addition to telemetry, the tool has power lines to carry electrical power supply signals generated by a surface-located power source for supply to the data processor and the sensor apparatus. FIG. 6B schematically shows the sensor apparatus is integrated as part of Schlumberger's Westbay System™, which is a multiple level monitoring tool that employs two sets of dual packers. With the packers in a fully expanded state, the tool may be positioned at the center of the wellbore with a small section hydraulically isolated from the rest of the wellbore fluid. The sensor apparatus of the present invention can be located in between the packers for analyzing the carbon dioxide concentration of the formation fluid communicating to the wellbore. This tool also includes a data processor and a telemetry bus (not shown). The data processor interfaces to the sensor to perform the data processing operations that determine carbon dioxide concentration as a function of the infrared intensity measurements carried out by the sensor apparatus. The telemetry bus communicates data and control signals between the data processor and a surface-located includes provision for receiving and distributing power provided from the surface.

There have been described and illustrated herein several embodiments of an optical sensor apparatus (and corresponding method) for measuring the concentration of carbon dioxide dissolved in a liquid solution. While particular embodiments of the invention have been described, it is not intended that the invention be limited thereto, as it is intended that the invention be as broad in scope as the art will allow and that the specification be read likewise. Thus, while particular optical configurations and processing parameters have been disclosed, it will be appreciated that other such optical configurations and processing parameters can be used as well. In addition, while particular types of broadband infrared light sources have been disclosed, it will be understood that narrowband infrared laser or light emitting diode (LED) sources can be used as well. Also, while preferred materials and trapezoidal geometries of the sensor's crystal have been shown, it will be recognized that other suitable optically dense materials and geometries can be used. Moreover, while particular configurations have been disclosed in reference to the response models and the calibration process for deriving the response model, it will be appreciated that other response models and calibration processes could be used as well. Finally, while the apparatus and method of the present invention is particularly suited for the monitoring of carbon dioxide sequestered in a subterranean formation (such as a brine water aquifer), and most particularly for wellbore monitoring of such sequestered carbon dioxide, it can also be used for measurement of carbon dioxide dissolved in a liquid solution for other applications. It will therefore be appreciated by those skilled in the art that yet other modifications could be made to the provided invention without deviating from its spirit and scope as claimed.

What is claimed is:

1. A downhole sensor for monitoring carbon dioxide dissolved in a liquid solution within a reservoir or an aquifer, the sensor comprising:
    a housing that defines a cavity;
    a cover;
    a crystal that comprises:
        a non-planar section having at least three surfaces for internally reflecting infrared radiation; and
        a base section having a bottom surface and a top surface;
    a sample chamber that surrounds at least part of the crystal, wherein the sample chamber is adapted such that, in use, the liquid solution under pressure characteristic of reservoir conditions is in direct contact with the at least three surfaces of the crystal and the at least three surfaces form an interface between the crystal and the liquid solution;
    a washer located between the cover and the top surface of the base section of the crystal, wherein the washer provides a seal between the cover and the crystal to isolate the sample chamber from the cavity defined by the housing;
    an infrared light source that directs at least one beam of infrared radiation into the crystal through the bottom surface of the base section so that the beam undergoes an attenuated internal reflection at each of the at least three surfaces of the crystal and then passes out of the bottom surface of the base section of the crystal, wherein the infrared light source is located within the cavity defined by the housing;
    an infrared detector that detects attenuated reflected infrared radiation produced by the crystal and that passes out of the base section of the crystal, wherein the infrared detector is located within the cavity defined by the housing;
    a signal processor, operably coupled to the infrared detector, that measures intensity of the attenuated reflected infrared radiation detected by the infrared detector; and
    a data processor, operably coupled to the signal processor, that determines concentration of carbon dioxide dissolved in the liquid solution from the intensity of the attenuated reflected infrared radiation measured by the signal processor.

2. A sensor according to claim 1, wherein:
    the infrared source is realized by a broadband infrared light source that generates a broadband infrared beam, and the infrared detector comprises a plurality of optical filters that provide bandpass optical filtering for predetermined infrared measurement bands.

3. A sensor according to claim 2, wherein:
    the broadband infrared beam emitted by the broadband infrared light source includes infrared radiation in a predetermined absorption band as well as infrared radiation in a predetermined reference band, and the optical filters provide bandpass optical filtering in predetermined infrared measurement bands corresponding to the predetermined absorption band and the predetermined reference band.

4. A sensor according to claim 3, wherein:
the predetermined absorption band is selected such that carbon dioxide has a relatively high absorbance as compared to the absorbance of water for infrared radiation within the predetermined absorption band; and
the predetermined reference band is selected such that carbon dioxide has minimal absorbance of infrared radiation within the predetermined reference band.

5. A sensor according to claim 3, wherein:
the predetermined absorption band is centered about 4.27 µm.

6. A sensor according to claim 3, wherein:
the predetermined reference band is centered about a wavelength selected from 4.00 µm and 5.00 µm.

7. A sensor according to claim 3, wherein:
the broadband infrared beam emitted by the broadband infrared light source includes infrared radiation in an additional reference band that is used to determine the presence of water in the liquid solution, and the plurality of optical filters provide bandpass optical filtering in a measurement band corresponding to the additional reference band.

8. A sensor according to claim 7, wherein:
the additional reference band is centered about 3.00 µm.

9. A sensor according to claim 2, wherein:
the broadband infrared light source comprises a resistive heating element integrated onto a thin dielectric membrane which is suspended on a micro-machined silicon structure.

10. A sensor according to claim 2, wherein:
the broadband infrared light source comprises a parabolic reflector that collimates infrared light generated by an infrared light emitting element into an infrared beam.

11. A sensor according to claim 1, further comprising:
a fluid chamber fluidly coupled to the sample chamber and spaced apart from the crystal, wherein the fluid chamber provides for headspace to accommodate for pressure variations in the sample chamber.

12. A sensor according to claim 1, further comprising:
a heat sink, operably coupled to the infrared detector, that dissipates heat away from the infrared detector.

13. A sensor according to claim 12, wherein:
the heat sink provides for passive heat dissipation.

14. A sensor according to claim 1, wherein:
the housing maintains structural integrity in pressure environments up to 50 MPa.

15. A sensor according to claim 1, wherein:
the data processor employs a response model that relates intensities of the attenuated reflected infrared radiation in predetermined measurement bands to the concentration of carbon dioxide dissolved in the liquid solution.

16. A sensor according to claim 15, wherein:
the response model is derived from a calibration process that measures a plurality of parameters.

17. A sensor according to claim 16, wherein:
the liquid solution comprises water, and the plurality of temperature dependent parameters include a parameter $k_1$, a parameter $k_2$, a parameter $k_4$, and a parameter $k_6$, a parameter $\alpha$ and a parameter $\beta$;
wherein the parameter $k_1$ is related to the absorbance of water in a predetermined reference band;
wherein the parameter $k_2$ is related to a reference intensity in the predetermined reference band and a reference intensity in a predetermined absorption band;
wherein the parameter $k_4$ is related to the absorbance of water in the predetermined reference band and in the predetermined absorption band;
wherein the parameter $k_6$ is related to the absorption coefficient of carbon dioxide dissolved in water;
wherein the parameter $\alpha$ is $-k_6$;
where in the parameter $\beta$ is $-\ln k_3 + k_5$ and represents the ratio of absorbance at the predetermined absorption band and the predetermined reference band.

18. A sensor according to claim 1, wherein:
the liquid solution comprises water.

19. A sensor according to claim 1, wherein:
the liquid solution comprises brine.

20. A sensor according to claim 1, wherein:
the liquid solution comprises hydrocarbons.

21. A downhole logging tool comprising the sensor of claim 1.

22. A sensor of claim 1, wherein the washer comprises a polymer.

23. A sensor of claim 22, wherein the washer comprises a polyether ether ketone.

24. A sensor of claim 1, wherein crystal comprises sapphire.

25. A method of monitoring carbon dioxide dissolved in a liquid solution comprising a liquid, the method comprising:
deploying a sensor in a wellbore, wherein the sensor comprises a crystal and a sample chamber;
introducing the liquid solution into the sample chamber of the sensor such that the liquid solution is in direct contact with the crystal of the sensor;
directing at least one beam of infrared radiation at a wavelength within a predetermined absorption band and at a wavelength within a predetermined reference band into the crystal for at least one attenuated internal reflection at an interface between the crystal and the liquid solution;
detecting attenuated reflected infrared radiation produced by the crystal;
measuring intensity of the detected attenuated reflected infrared radiation within the absorption band ($I_{c2}$);
measuring intensity of the detected attenuated reflected infrared radiation within the reference band ($I_{c1}$); and
determining the concentration of carbon dioxide ($C_c$) dissolved in the liquid solution using (i) the intensity of the detected attenuated reflected infrared radiation within the absorption band ($I_{c2}$), (ii) the detected attenuated reflected infrared radiation within the reference band ($I_{c1}$), and (iii) a temperature of the liquid solution (T), wherein the determining comprises employing a response model that relates (i) the intensity of the detected attenuated reflected infrared radiation within the absorption band ($I_{c2}$) and (ii) the detected attenuated reflected infrared radiation within the reference band ($I_{c1}$) to the concentration of carbon dioxide dissolved in the liquid solution according to:

$$C_c = \frac{\ln \frac{I_{c2}}{I_{c1}} - \beta(T)}{\alpha(T)}$$

wherein the parameter $\alpha(T)$ is $-k_6(T)$;
wherein the parameter $\beta(T)$ is $-\ln k_3(1)+k_5(T)$ and represents the ratio of absorbance at the predetermined absorption band and the predetermined reference band;
wherein $k_3(T)$ is $k_2(T)/k_1(T)$;
wherein $k_5(T)$ is $-\ln (k_4(T)/k_3(T))$;
wherein the parameter $k_1(T)$ is related to the absorbance of the liquid in the predetermined reference band as a function of temperature;
wherein the parameter $k_2(T)$ is related to a reference intensity in the predetermined reference band and a reference intensity in the predetermined absorption band as a function of temperature;
wherein the parameter $k_4((T))$ is related to the absorbance of the liquid in the predetermined reference band and in the predetermined absorption band as a function of temperature; and
wherein the parameter $k_6((T))$ is related to the absorption coefficient of carbon dioxide dissolved in the liquid as a function of temperature.

26. A method according to claim 25, wherein:
the at least one beam of infrared radiation comprises a broadband infrared beam, and the detecting includes bandpass optical filtering for the predetermined absorption band and the predetermined reference band.

27. A method according to claim 26, wherein:
the at least one broadband infrared beam includes infrared radiation in the predetermined absorption band as well as infrared radiation in the predetermined reference band, and the bandpass optical filtering is provided in predetermined infrared measurement bands corresponding to the predetermined absorption band and the predetermined reference band.

28. A method according to claim 27, wherein:
the predetermined absorption band is selected such that carbon dioxide has a relatively high absorbance as compared to the absorbance of water for infrared radiation within the predetermined absorption band; and
the predetermined reference band is selected such that carbon dioxide has minimal absorbance of infrared radiation within the predetermined reference band.

29. A method according to claim 27, wherein:
the predetermined absorption band is centered about 4.27 µm.

30. A method according to claim 27, wherein:
the predetermined reference band is centered about a wavelength selected from 4.00 µm and 5.00 µm.

31. A method according to claim 27, wherein:
the broadband infrared beam includes infrared radiation in an additional reference band that is used to determine the presence of water in the liquid solution, and the bandpass optical filtering is provided in a measurement band corresponding to the additional reference band.

32. A method according to claim 31, wherein:
the additional reference band is centered about 3.00 µm.

33. A method according to claim 26, wherein:
the broadband infrared beam is generated by a broadband infrared light source comprising a resistive heating element integrated onto a thin dielectric membrane which is suspended on a micro-machined silicon structure.

34. A method according to claim 26, wherein:
the broadband infrared beam is generated by a broadband infrared light source having a parabolic reflector that collimates infrared light generated by an infrared light emitting element into an infrared beam.

35. A method according to claim 25, wherein:
the crystal has a base section with a lip and a trapezoidal section, wherein the trapezoidal section is surrounded by the sample chamber and defines at least one interface that provides for attenuated internal reflection of the infrared beam and the lip enables the provision for a pressure seal.

36. A method according to claim 35, wherein:
the trapezoidal section provides for a sequence of three attenuated internal reflections of the infrared beam.

37. A method according to claim 25, wherein:
the sensor comprises a housing that maintains structural integrity in pressure environments in the range from 0 MPa to 50 MPa.

38. A method according to claim 25, wherein:
the response model is derived from a calibration process that measures parameter $k_1(T)$, parameter $k_2(T)$, parameter $k_4(T)$, and parameter $k_6(T)$.

39. A method according to claim 25, wherein:
the liquid is water.

40. A method according to claim 25, wherein:
the liquid solution comprises brine.

41. A method according to claim 25, wherein:
the liquid solution comprises hydrocarbons.

42. A method according to claim 25, wherein:
the crystal and the sample chamber are realized as part of a downhole logging tool that performs downhole sampling of the liquid solution as well as downhole fluid analysis for determining carbon dioxide dissolved in the sampled liquid solution.

43. A method according to claim 25, wherein:
the liquid solution is acquired from a subterranean location for monitoring carbon dioxide sequestered in a subterranean formation.

44. A method according to claim 43, wherein:
the subterranean location is disposed within the subterranean formation.

45. A method according to claim 43, wherein:
the subterranean location is disposed above the subterranean formation.

46. A method according to claim 43, wherein:
the subterranean location is within an observation well that extends into the subterranean formation.

47. A method according to claim 43, wherein:
the subterranean formation comprises a salt water aquifer.

48. A method according to claim 47, wherein:
the subterranean location is within a drinking water aquifer disposed above the salt water aquifer.

49. A method according to claim 47, wherein:
the method is repeated for multiple sensors spaced apart from one another.

50. A method of claim 25, wherein:
the crystal comprises a base section and the at least one beam of infrared radiation passes into the crystal through the base section, is reflected internally, and passes out of the base section.

* * * * *